(12) United States Patent
Naeymi-Rad et al.

(10) Patent No.: US 7,167,858 B2
(45) Date of Patent: Jan. 23, 2007

(54) IDENTIFICATION MAPPING AND TRANSLATION METHOD

(75) Inventors: Frank Naeymi-Rad, Libertyville, IL (US); David Alvin, Glen Ellyn, IL (US); David Pilkington, Wildwood, IL (US); Regis Charlot, Lake Bluff, IL (US)

(73) Assignee: Intelligent Medical Objects, Inc., Northbrook, IL (US)

( * ) Notice: Subject to any disclaimer, the term of this patent is extended or adjusted under 35 U.S.C. 154(b) by 529 days.

(21) Appl. No.: 10/642,072

(22) Filed: Aug. 15, 2003

(65) Prior Publication Data

US 2005/0038671 A1 Feb. 17, 2005

(51) Int. Cl.
*G06F 17/30* (2006.01)
(52) U.S. Cl. .......................... 707/6; 707/100
(58) Field of Classification Search ........ 707/100–104, 707/1–10, 200–205
See application file for complete search history.

(56) References Cited

U.S. PATENT DOCUMENTS

| | | | |
|---|---|---|---|
| 5,903,889 A | 5/1999 | de la Huerga | |
| 6,246,794 B1 * | 6/2001 | Kagehiro et al. | 382/185 |
| 6,901,398 B1 * | 5/2005 | Horvitz et al. | 707/5 |
| 6,987,221 B1 * | 1/2006 | Platt | 84/601 |
| 2001/0051880 A1 | 12/2001 | Schurenberg | |
| 2002/0007284 A1 | 1/2002 | Schurenberg | |
| 2003/0088438 A1 * | 5/2003 | Maughan et al. | 705/2 |

OTHER PUBLICATIONS

Gill, Leicester E, OX-LINK: The Oxford Medical Record Linkage System, 1997, Oxford University Press, Chapter 2.*
Naeymi-Rad, F., Carmony, L., Trace, D., Georgakis, C., and Weil, M. H. 1988. A relational database design in support of standard medical terminology in multi-domain knowledge bases. In Proceedings of the 1988 ACM SIGMOD international Conference on Management of Data (Chicago, Illinois, United States, Jun. 1-3, 1988). H. Boral and P. Larson, Eds.*
Seligman, L. and Rosenthal, A. ☐XML☐s impact on databases and data sharing,☐ Computer, Jun. 2001, p. 59-67.*
Frank Fariborz Naeymi-Rad, "A Featured Dictionary to Support Database Translation, Information Retrieval, Intelligent Medical Records, and Expert Systems", May 1990, Chicago, IL.

* cited by examiner

*Primary Examiner*—Mohammad Ali
(74) *Attorney, Agent, or Firm*—Beem Patent Law Firm

(57) ABSTRACT

A method for mapping and identifying entity information in a system that includes a database. A client application sends client entity attributes to the system that includes a database The system compares the attributes of the client entity with each of the system entities stored in the system database. Based on the results of the comparison, a score is calculated for the relevance between the client entity and each entity stored in the system. To perform this calculation, a multi-membership Bayesian function is used. Once the scores are computed, they are classified into three confidence zones based on predetermined threshold values. The client attributes are inserted into the system database. These attributes then are connected either to an existing system entity, or are connected to a new system entity that is created.

10 Claims, 18 Drawing Sheets

| | TRANSACTION | | |
|---|---|---|---|
| COLUMN | DATA TYPE | NULL? | PURPOSE |
| TRANSACTION_CODE | NUMBER(10) | N | Primary key; values are assigned from sequence TRANSACTION_SEQ |
| SYSTEM_USER_CODE | NUMBER(10) | N | Foreign key to SYSTEM_USER table; cascading delete; indicates user who initiated the transaction |
| WEIGHT_GROUP_CODE | NUMBER(10) | N | Foreign key to WEIGHT_GROUP table; cascading delete; indicates weight group to consult for default prevalence, P, and Pbar values when creating new entities |
| HIGH_THRESHOLD | NUMBER(5,4) | N | Value at or above which the transaction zone is considered green |
| LOW_THRESHOLD | NUMBER(5,4) | N | Value at or below which the transaction zone is considered red |
| ZONE | VARCHAR2(1) | Y | Indicator of zone from which best matching entity came; values are:<br>• R: red<br>• Y: yellow<br>• G: green |
| DATE_CREATED | DATE | N | Date and time of row creation |

NOTES
Each row in the TRANSACTION table contains information supplied by the inquiry, as well as the zone resulting from the scoring process for the client entity associated with the transaction. Rows are deleted upon completion of the transaction (receipt of a decision send message).

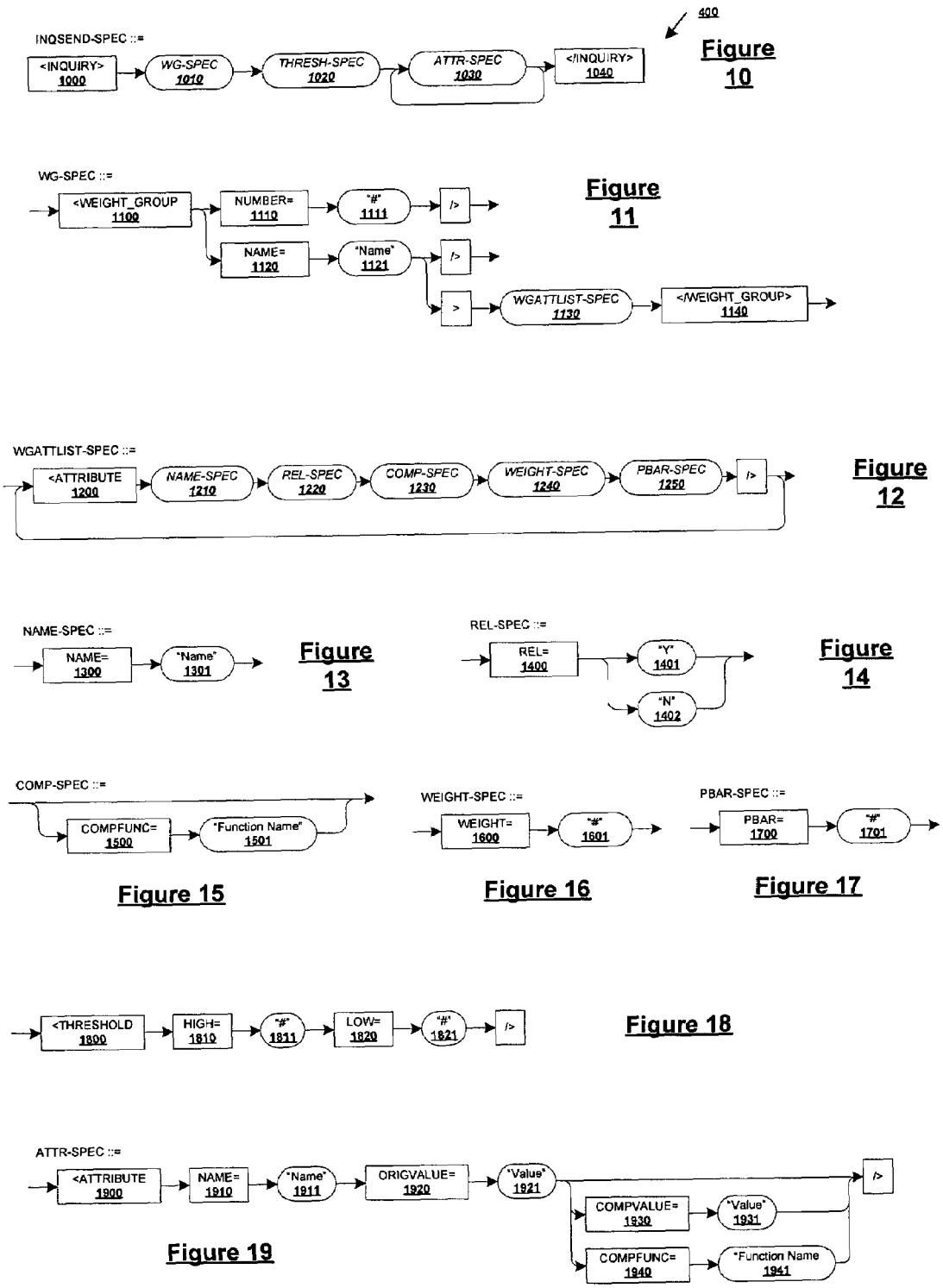

Figure 20
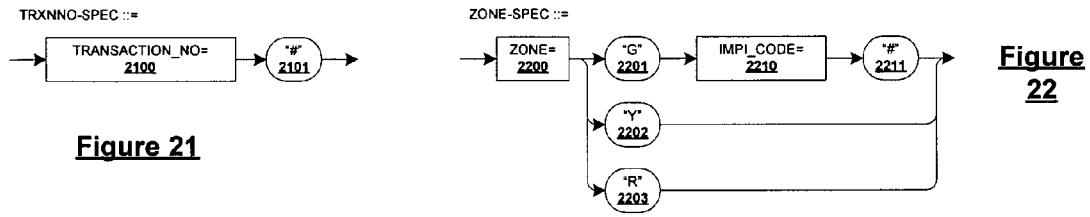
Figure 21
Figure 22
Figure 23
Figure 24
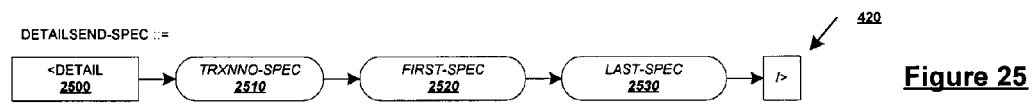
Figure 25
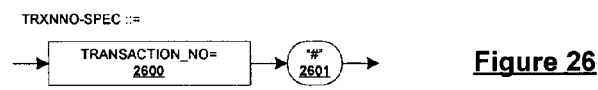
Figure 26
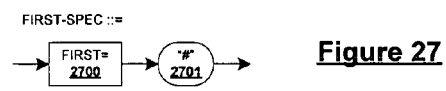
Figure 27
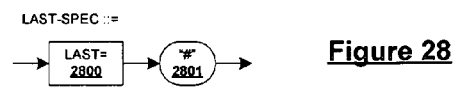
Figure 28

Figure 47:

| COLUMN | WEIGHT_GROUP DATA TYPE | NULL? | PURPOSE |
|---|---|---|---|
| WEIGHT_GROUP_CODE | NUMBER(10) | N | Primary key; values are assigned from sequence WEIGHT_GROUP_SEQ |
| NAME | VARCHAR2(100) | N | Unique description of the group's purpose or source of data |
| DEFAULT_PREVALENCE | NUMBER(5,4) | N | Value between 0 and 1. Value is copied to the ENTITY table upon creation of a new entity. |
| DATE_CREATED | DATE | N | Date and time of row creation |
| DATE_UPDATED | DATE | N | Date and time of last update to row |

| NOTES |
|---|
| The WEIGHT_GROUP table serves to group weight sets together in order to provide default PREVALENCE values when new entities are created. Default P and PBAR values are stored for the group in the WEIGHT_ATTRIBUTE table below. |

Figure 48:

| WEIGHT_ATTRIBUTE | | | |
|---|---|---|---|
| COLUMN | DATA TYPE | NULL? | PURPOSE |
| WEIGHT_GROUP_CODE | NUMBER(10) | N | Foreign key to WEIGHT_GROUP |
| ATTRIBUTE_NAME | VARCHAR2(20) | N | Name of attribute, must be unique within each WEIGHT_GROUP_CODE |
| RELEVANCE_FLAG | NUMBER(1) | N | Flag (0 or 1) to indicate whether attribute should be placed in the subset of attributes defined as most relevant. See Scoring Algorithm section for more details. Default value is 0. |
| COMPARISON_FUNCTION | VARCHAR2(128) | Y | Indicator of function to use (if any) in converting DISPLAY_VALUE value to COMPARISON_VALUE. If none specified, values will be identical. Functions are built into Impi core libraries. |
| RELATIVE_WEIGHT | NUMBER(3) | N | Positive integer that represents a weight relative to other attributes within the group; higher weights indicate attributes that contribute more toward posterior probability. Default value is 0. Range must be between 0 and 999. |
| DEFAULT_P | NUMBER(5,4) | N | Default computed contribution of the attribute within a group when a match is made on the attribute's value. Value is equal to the attribute's weight divided by the sum of weights for the group. Value is between 0 and 1. Value is copied to ATTRIBUTE_COMPUTATION_VALUE table upon creation of a new entity. |
| DEFAULT_PBAR | NUMBER(5,4) | N | Manually set default contribution of the attribute within a group when a match is not made. Value is between 0 and 1. Value is copied to ATTRIBUTE_COMPUTATION_VALUE table upon creation of a new entity. |
| DATE_CREATED | DATE | N | Date and time of row creation |
| DATE_UPDATED | DATE | N | Date and time of last update to row |

| NOTES |
|---|
| The WEIGHT_ATTRIBUTE table serves to indicate relative importance of attributes within weight groups, and provides default P and PBAR values of attributes when new entities are created. |
| This table also indicates what attributes are to be involved for any transaction that uses the weight group, and which attributes are the most relevant (i.e., compared first). |

Figure 49:

| COLUMN | DATA TYPE | NULL? | ENTITY<br>PURPOSE |
|---|---|---|---|
| ENTITY_CODE | NUMBER(10) | N | Primary key; values are assigned from sequence ENTITY_SEQ |
| PREVALENCE | NUMBER(5,4) | N | Value between 0 and 1. Starting point of all probability computations for this entity. |
| DATE_CREATED | DATE | N | Date and time of row creation |

| NOTES |
|---|
| The ENTITY table simply controls creation of new entities. It is simply a repository for the code numbers in order to allow referential integrity constraints to prevent orphaned data in the ATTRIBUTE and ATTRIBUTE_COMPUTATION_VALUE tables. |

Figure 50:

| COLUMN | DATA TYPE | ATTRIBUTE<br>NULL? | PURPOSE |
|---|---|---|---|
| ATTRIBUTE_CODE | NUMBER(10) | N | Primary key; values are assigned from sequence ATTRIBUTE_SEQ |
| ENTITY_CODE | NUMBER(10) | N | Foreign key to ENTITY table; cascading delete |
| ATTRIBUTE_NAME | VARCHAR2(20) | N | Name of attribute |
| ATTRIBUTE_GROUP_CODE | NUMBER(10) | N | Since it is expected that attributes will be added for an entity over time, this code will logically group attribute values (assigned from sequence ATTRIBUTE_GROUP_SEQ) together for display purposes. |
| ORIGINAL_VALUE | VARCHAR2(4000) | N | Original value of attribute, as copied from TRANSACTION_ATTRIBUTE table |
| COMPARISON_VALUE | VARCHAR2(4000) | Y | Potentially modified value from ORIGINAL_VALUE stored for comparison purposes; value is copied from the COMPARISON_VALUE column or derived from the ORIGINAL_VALUE column in the TRANSACTION_ATTRIBUTE table |
| TRANSACTION_CODE | NUMBER(10) | Y | Unique number of transaction that created this row. Useful for backout and cleanup purposes |
| DATE_CREATED | DATE | N | Date and time of row creation |
| DATE_UPDATED | DATE | N | Date and time of last update to row |

| NOTES |
|---|
| The ATTRIBUTE table contains values of each attribute associated with an entity. Attributes are grouped together logically according to the event when they were inserted. |

Figure 51:

| ATTRIBUTE_COMPUTATION_VALUE | | | |
|---|---|---|---|
| COLUMN | DATA TYPE | NULL? | PURPOSE |
| ENTITY_CODE | NUMBER(10) | N | Foreign key to ENTITY table; cascading delete |
| ATTRIBUTE_NAME | VARCHAR2(100) | N | Name of attribute |
| RELATIVE_WEIGHT | NUMBER(3) | N | Positive integer that represents a weight relative to other attributes within the group; higher weights indicate attributes that contribute more toward posterior probability. Default value is 0. Range must be between 0 and 999. |
| COMPARISON_FUNCTION | VARCHAR2(128) | Y | Indicator of function to use (if any) in converting DISPLAY_VALUE value to COMPARISON_VALUE for all attributes of this name for this entity. If none specified, values will be identical or as indicated via transaction. Value is obtained either from TRANSACTION_ATTRIBUTE if explicitly identified in transaction, or from WEIGHT_ATTRIBUTE otherwise |
| P | NUMBER(5,4) | N | Positive contribution of this attribute to probability computations for this entity. Value is copied from DEFAULT_P column in WEIGHT_ATTRIBUTE table |
| PBAR | NUMBER(5,4) | N | Negative contribution of this attribute to probability computations for this entity. Value is copied from DEFAULT_PBAR column in WEIGHT_ATTRIBUTE table |
| DATE_CREATED | DATE | N | Date and time of row creation |
| DATE_UPDATED | DATE | N | Date and time of last update to row |

| NOTES |
|---|
| The ATTRIBUTE_COMPUTATION_VALUE table contains values for use in probability computations for the associated entity. |

Figure 52:

| COLUMN | TRANSACTION DATA TYPE | NULL? | PURPOSE |
|---|---|---|---|
| TRANSACTION_CODE | NUMBER(10) | N | Primary key; values are assigned from sequence TRANSACTION_SEQ |
| SYSTEM_USER_CODE | NUMBER(10) | N | Foreign key to SYSTEM_USER table; cascading delete; indicates user who initiated the transaction |
| WEIGHT_GROUP_CODE | NUMBER(10) | N | Foreign key to WEIGHT_GROUP table; cascading delete; indicates weight group to consult for default prevalence, P, and Pbar values when creating new entities |
| HIGH_THRESHOLD | NUMBER(5,4) | N | Value at or above which the transaction zone is considered green |
| LOW_THRESHOLD | NUMBER(5,4) | N | Value at or below which the transaction zone is considered red |
| ZONE | VARCHAR2(1) | Y | Indicator of zone from which best matching entity came; values are:<br>• R: red<br>• Y: yellow<br>• G: green |
| DATE_CREATED | DATE | N | Date and time of row creation |

| NOTES |
|---|
| Each row in the TRANSACTION table contains information supplied by the inquiry, as well as the zone resulting from the scoring process for the client entity associated with the transaction. Rows are deleted upon completion of the transaction (receipt of a decision send message). |

Figure 53:

| COLUMN | TRANSACTION_ATTRIBUTE DATA TYPE | NULL? | PURPOSE |
|---|---|---|---|
| TRANSACTION_CODE | NUMBER(10) | N | Foreign key to TRANSACTION table; cascading delete |
| ATTRIBUTE_NAME | VARCHAR2(20) | N | Name of attribute. Attribute names should be unique for each transaction |
| ORIGINAL_VALUE | VARCHAR2(4000) | N | Contains original value of attribute |
| COMPARISON_FUNCTION | VARCHAR2(128) | Y | Name of function to apply to value of ORIGINAL_VALUE in order to obtain value for COMPARISON_VALUE. If null, COMPARISON_VALUE will be set equal to ORIGINAL_VALUE |
| COMPARISON_VALUE | VARCHAR2(4000) | Y | Value after modification algorithm has been applied to ORIGINAL_VALUE; this value is compared to COMPARISON_VALUE in ATTRIBUTE table during scoring process |
| DATE_CREATED | DATE | N | Date and time of row creation |

| NOTES |
|---|
| The TRANSACTION_ATTRIBUTE table contains one or more rows for every row in the TRANSACTION table. Data elements are inserted in separate rows within this table and labeled by attribute names. |

Figure 54:

| | TRANSACTION_RESULT | | |
|---|---|---|---|
| COLUMN | DATA TYPE | NULL? | PURPOSE |
| TRANSACTION_CODE | NUMBER(10) | N | Foreign key to TRANSACTION table; cascading delete |
| ENTITY_CODE | NUMBER(10) | N | Foreign key to ENTITY table; cascading delete |
| POSTERIOR_PROBABILITY | NUMBER(5,4) | N | Probability that the entity described by transaction matches the known entity. Value must be between 0 and 1, inclusive |
| RESULT_INDEX | NUMBER(10) | N | Rank within all results for this transaction, in descending order of POSTERIOR_PROBABILITY |
| DATE_CREATED | DATE | N | Date and time of row creation |

| NOTES |
|---|
| The TRANSACTION_RESULTS table contains the results of scoring transactions. Each transaction may have several rows placed in this table during a scoring process. |

| Side by Side Comparison | | | | |
|---|---|---|---|---|
| Entity code: 567 | Posterior probability: 0.9508 | | | |
| Known Entities | | | Your Data | |
| Attribute | Value | | Attribute | Value |
| ADDRESS1 | 6 Feet Under Way | | ADDRESS1 | 6 Feet Under Way |
| CITY | Tombstone | | CITY | Tombstone |
| DOB | 03/28/1986 | | DOB | 03/28/1986 |
| EMP_SSN | 000-00-8686 | | EMP_SSN | 000-00-8686 |
| FIRSTNAME | Mort | | FIRSTNAME | Mort |
| GENDER | M | | GENDER | M |
| LASTNAME | Tality | | LASTNAME | Tality |
| PHONE | (555) 555-1234 | | PHONE | (555) 555-1234 |
| RELATION | Dependent | | RELATION | Dependent |
| REL_SSN | 999-99-8686 | | REL_SSN | 999-99-8686 |
| STATE | AZ | | STATE | AZ |
| ZIP | 87654 | | ZIP | 87654 |

Figure 59

| Side by Side Comparison | | | | |
|---|---|---|---|---|
| Entity code: 568 | Posterior probability: 0.8370 | | | |
| Known Entities | | | Your Data | |
| Attribute | Value | | Attribute | Value |
| ADDRESS1 | 6 Feet Under Way | | ADDRESS1 | 6 Feet Under Way |
| CITY | Tombstone | | CITY | Tombstone |
| DOB | 03/28/1986 | | DOB | 03/28/1986 |
| EMP_SSN | 000-00-8686 | | EMP_SSN | 000-00-8686 |
| FIRSTNAME | Faye | | FIRSTNAME | Mort |
| GENDER | M | | GENDER | M |
| LASTNAME | Tality | | LASTNAME | Tality |
| PHONE | (555) 555-1234 | | PHONE | (555) 555-1234 |
| RELATION | Dependent | | RELATION | Dependent |
| REL_SSN | 999-99-8686 | | REL_SSN | 999-99-8686 |
| STATE | AZ | | STATE | AZ |
| ZIP | 87654 | | ZIP | 87654 |

Figure 60

IDENTIFICATION MAPPING AND TRANSLATION METHOD

BACKGROUND OF THE INVENTION

1. Field of the Invention

The present invention is a method for mapping and identifying entity information in a system that includes a database.

2. Description of the Related Art

In the world of information technology, great consequence rests on the ability to uniquely identify a data entity within the context of a population of data. Whether this data exists within the realm of marketing, finance, education, medicine or some other field, the concept of an identity represented by data elements is fundamental to the vast majority of applications upon which computing power is applied. At the intersection of commerce, global population growth, health care and privacy issues, there is a basic need for the demonstrated ability to distinguish between one entity and another with reliable and predictable results despite shifting data values.

These entity matching tasks are often completed with a master patient index (MPI) and associated applications. An MPI is well known and utilized in the healthcare industry. As healthcare systems become increasingly complex and distributed over wide areas, it is important to be able to uniquely and correctly identify individual patients over a wide array of disjoint or unconnected systems.

Medsphere, QuadraMed and IBM all have developed MPI systems. Current MPI systems seek to uniquely identify an individual based on information provided. Often this information centers on demographic data, and can be sparse or outdated, which can lead to the discontinuity or loss of important patient data. Current MPI systems take information provided and perform pattern-matching comparisons with persons already known to the system. The pattern-matching algorithms employed make probabilistic determinations based on the relevance of certain data points or attributes. Some attributes are more valuable than others in determining a match, and so potential matches on highly relevant attributes necessarily increase the likelihood of a correct match. Once an MPI system is consulted and a match is made, previously stored patient information are retrieved with confidence that it is the proper information for the patient in question.

Pattern Matching algorithm for Symptom-Disease Matching Incorporated by Reference Pattern matching algorithms are used to match two sets of data. For example a multi-membership Bayesian algorithm can be implemented to match a set of medical symptoms to a disease. The multi-membership Bayesian algorithm to perform this symptom-disease matching is disclosed by "A Feature Dictionary To Support Database Translation, Information Retreival, Intelligent Medical Records, and Expert Systems" by Frank Fariborz Naeymi-Rad, and is incorporated by reference as if fully reproduced herein.

An efficient and accurate MPI system should identify a match or a lack of a match with a large enough confidence as to eliminate the need for human intervention. Current MPI systems do not use adequate pattern-matching algorithms, as there is still need for extensive human intervention. As a system stores patient information, the confidence of a positive or negative match increases. Current MPI systems do not increase confidence fast enough and therefore are inefficient. Also, because the confidence of matching is not high, inaccurate results occur. Therefore it is desired that an efficient and accurate MPI system and pattern-matching algorithm be developed.

Furthermore, current MPI systems are geared exclusively toward the healthcare industry. Due to this, the attributes used to describe the entities are specific to healthcare related attributes. Therefore, current MPI systems cannot be used by other industries that seek to identify a data entity represented by data elements.

BRIEF SUMMARY OF THE INVENTION

A method for mapping and identifying entity information utilizes a computational algorithm and a system that includes a database. Several steps are included in the method preferably in the following order. A client application sends client entity attributes to the system. The system compares the attributes of the client entity with each of the system entities stored in the system database. Based on the results of the comparison, a score is calculated for the relevance between the client entity and each entity stored in the system. To perform this calculation, a multi-membership Bayesian function is used. Once the scores are computed, they are classified into preferably three confidence zones based on predetermined threshold values. The client attributes are inserted into the system database. These attributes are connected either to an existing system entity or to a new system entity.

In one embodiment, the communications protocol used to send information to and from the system is an XML communications protocol. The multi-membership Bayesian calculation function may utilize positive, negative and neutral contributions to the scores. The client entities and system entities are particularly advantageous in representing people, who tend to have complex characteristics.

BRIEF DESCRIPTION OF THE DRAWINGS

FIG. 10 is a railroad diagram detailing the formation of an inquiry send XML message.

FIG. 11 is a railroad diagram detailing the formation of XML code for a weight group specification.

FIG. 12 is a railroad diagram detailing the formation of XML code for weight group attribute list specification.

FIG. 13 is a railroad diagram detailing the formation of XML code for name specification.

FIG. 14 is a railroad diagram detailing the formation of XML code for relevance flag specification.

FIG. 15 is a railroad diagram detailing the formation of XML code for comparison function specification.

FIG. 16 is a railroad diagram detailing the formation of XML code for relative weight specification.

FIG. 17 is a railroad diagram detailing the formation of XML code for Pbar specification.

FIG. 18 is a railroad diagram detailing the formation of XML code for threshold values specification.

FIG. 19 is a railroad diagram detailing the formation of XML code for attribute specification.

FIG. 20 is a railroad diagram detailing the formation of XML code for inquiry receive messages.

FIG. 21 is a railroad diagram detailing the formation of XML code for transaction number specification.

FIG. 22 is a railroad diagram detailing the formation of XML code for zone specification.

FIG. 23 is a railroad diagram detailing the formation of XML code for quantity of results specification.

FIG. 24 is a railroad diagram detailing the formation of XML code for the weight group number specification.

FIG. 25 is a railroad diagram detailing the formation of XML code for detail send messages.

FIG. 26 is a railroad diagram detailing the formation of XML code for transaction number specification for detail send messages.

FIG. 27 is a railroad diagram detailing the formation of XML code for the first "record" number specification for detail send messages.

FIG. 28 is a railroad diagram detailing the formation of XML code for the last "record" number specification for detail send messages.

FIG. 47 is a detailed description of the "schema" for the weight group table.

FIG. 48 is a detailed description of the "schema" for the weight attribute table.

FIG. 49 is a detailed description of the "schema" for the entity table.

FIG. 50 is a detailed description of the "schema" for the attribute table.

FIG. 51 is a detailed description of the "schema" for the attribute computation value table.

FIG. 52 is a detailed description of the "schema" for the transaction table.

FIG. 53 is a detailed description of the "schema" for the transaction attribute table.

FIG. 54 is a detailed description of the "schema" for the transaction result table.

FIG. 59 is a screenshot showing a side by side comparison of a client entity and a known system entity.

FIG. 60 is a screenshot showing a side by side comparison of a client entity and a known system entity.

DETAILED DESCRIPTION OF THE INVENTION

1. Overview

Figure 1:
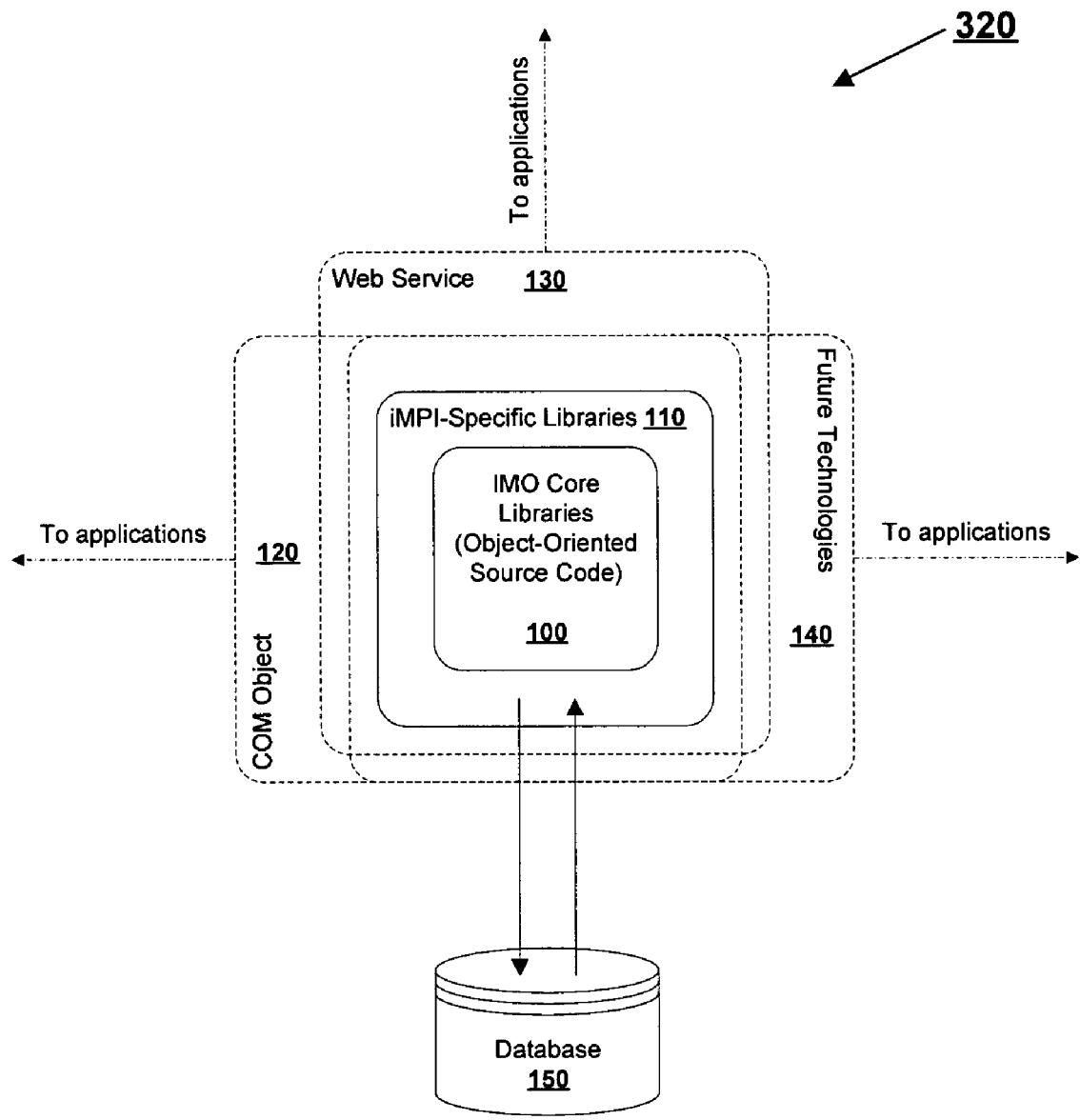
FIG. 1 is a diagram showing the overall architecture of the system.

The system includes a database and an interface such as a COM object or web service. Client applications communicate with the system through an XML communications protocol.

Method for Interfacing Applications Incorporated by Reference

An example of a client application is disclosed in the commonly assigned, patent application Ser. No. 10/642,108, titled IDENTIFICATION MAPPING AND TRANSLATION METHOD, having, filed contemporaneously herewith, the disclosure of which is incorporated herein by reference.

A client must log into the system before submitting requests for action. When a client application submits a message requesting some action, a new transaction record is inserted into the database. Since the transaction messages are tracked through the database, multiple client application messages can be handled by the system at once. Furthermore, the transaction results are stored dynamically providing efficiency and accuracy to the transaction.

If a client requests a runtime transaction, an inquiry message is sent to the system. This message specifies the attributes that are to be used for comparison. The client is able to select the attributes individually or request that a predefined attribute group be used. The client then sends the attribute values to the system for processing. First, the system converts the client attribute values into a format that is suitable for comparison. This conversion is performed either by copying over the attribute value as is or by applying a comparison function which formats the attribute value. The system then performs a comparison with each system entity using the subset of attribute values that the client has defined as key fields. To perform this comparison, a multi-membership Bayesian calculation function is used. The function utilizes both positive contributions for attribute matches and negative contributions for non-matches. The results of this function are scores which quantify the relevancy between the client and system entity.

Once a score is determined, the scores are classified and placed into one of three zones based on threshold values. The green zone indicates a high probability of a match; the red zone indicates a high probability of a non-match; and the yellow zone indicates the need for some client intervention. The client may be a human actor or an artificial intelligence device. These results are sent back to the client for consideration. The client then decides whether there is a match or a need to perform further calculation. If further calculation must be performed, the client sends more detail about the client entity to the system. The comparison calculations are again performed by the system and the results sent back to the client.

The client decides whether the client entity is already in the system. If the client entity is in the system, the attributes for this entity are inserted into the database and linked to the appropriate system entity. Each attribute value is assigned a positive and negative contribution value when inserted into the database. If the client entity is not in the system, the client entity is inserted as a new system entity. The attributes are inserted into the database and linked to this new system entity. Each attribute value is assigned a positive and negative contribution value. The client also can decide to abort the process at any point. Once the transaction is completed, the rows relevant to the transaction are removed from the transaction management tables.

The client can also perform administrative tasks. These tasks include listing information stored in the database concerning entities and attributes and adding or deleting entities and attributes.

The client logs out of the system when all tasks are completed.

2. System Overview

The present system 320, illustrated in FIG. 1, consists of a core library of object-oriented source code 100 which is supplemented by iMPI specific libraries 110 and inheritance of IMO-standard library objects. At the outer shell of the system 320 is an interface, such as a COM object 120, web service 130 or some future technology 140 through which interactions with client applications 330 occur. The system 320 further consists of a database 150 and interaction with the database 150 is handled through the object oriented libraries (100,110).

Figure 2:
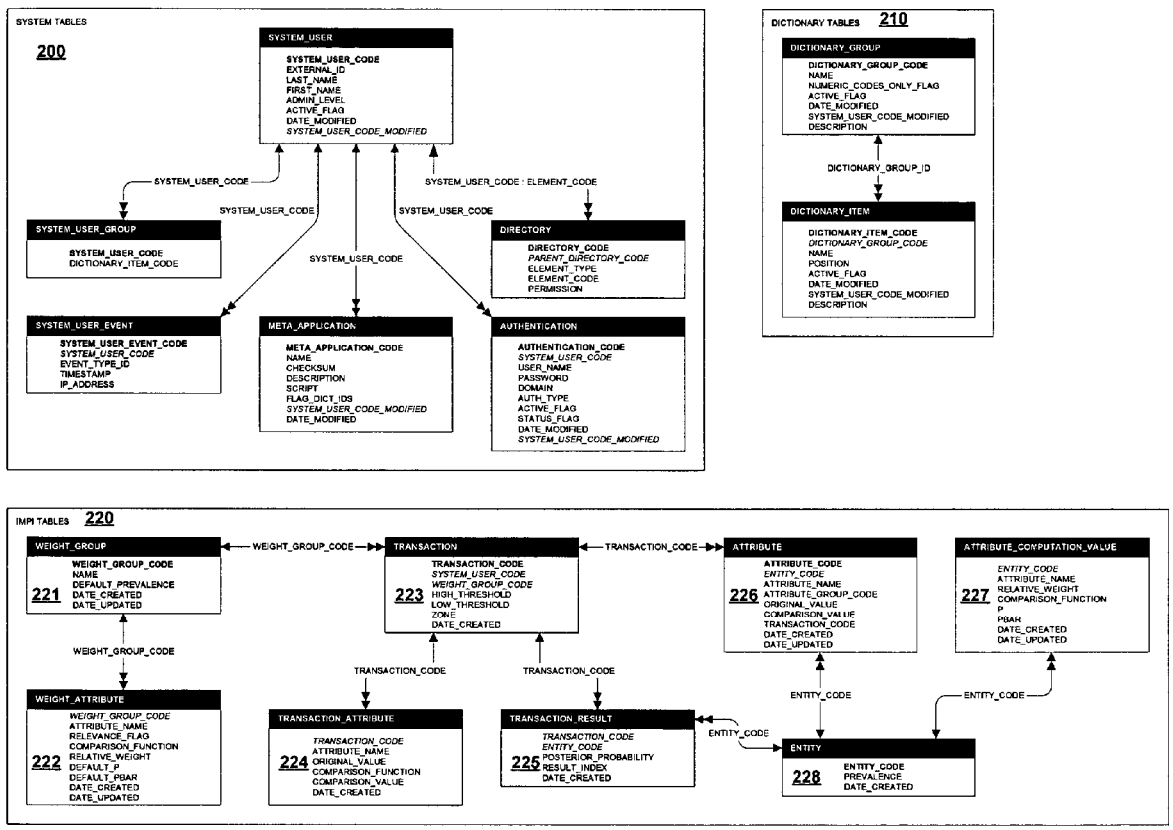
FIG. 2 is the database ER diagram showing the layout of the database.

The database 150, illustrated in FIG. 2, consists of three sets of tables. The first set is system tables 200 which contain information concerning user identification, authentication and event management. The second set is the dictionary tables 210. The last set is the iMPI tables 220 which store information for the transaction management, entity storage and weight group storage. In one embodiment, the system is a master patient index.

Adaptive Data Manager 09/997,723 Incorporated by Reference

Commonly assigned U.S. patent application Ser. No. 09/997,723, entitled Adaptive Data Manager, discloses an adaptive data manager (ADM) and is incorporated by reference as if fully reproduced herein. The ADM describes the system tables and dictionary tables utilized in the present system 320.

The transaction management tables are TRANSACTION 223, TRANSACTION_ATTRIBUTE 224 and TRANSACTION_RESULT 225. TRANSACTION 223 table contains information supplied through a client application 330 inquiry as well as the zone from which the best matching entity came. The zone is an indicator of the range in which the best, highest, score for a client entity falls. FIG. 52 shows the specific fields in the TRANSACTION table. TRANSACTION_ATTRIBUTE 224 table contains one or more rows for every row in the TRANSACTION 223 table and stores information about the attributes, such as original and comparison values. FIG. 53 shows the specific fields in the TRANSACTION_ATTRIBUTE table. The TRANSACTION_RESULT 225 table contains the results of the scoring process. Each transaction may have several rows placed in this table during a scoring process. FIG. 54 shows the specific fields in the TRANSACTION_RESULT table.

The entity storage tables are ENTITY 228, ATTRIBUTE 226 and ATTRIBUTE_COMPUTATION_VALUE 227. The ENTITY table 228 is simply a repository for the entity codes, which are unique IDs assigned to each entity in order to allow referential integrity constraints to prevent orphaned data in the other entity storage tables. FIG. 49 shows the specific fields in the ENTITY table. The ATTRIBUTE table 226 contains values of each attribute associated with an entity. Attributes are grouped together logically according to the event when they were inserted. FIG. 50 shows the specific fields in the ATTRIBUTE table. The ATTRIBUTE_COMPUTATION_VALUE 227 table contains values for use in the probability computations for the associated entity. FIG. 51 shows the specific fields in the ATTRIBUTE_COMPUTATION_VALUE table.

The weight group storage tables are WEIGHT_GROUP 221 and WEIGHT_ATTRIBUTE 222. The WEIGHT_GROUP table 221 groups weight sets together in order to provide default prevalence values when new entities are created. FIG. 47 shows the specific fields in the WEIGHT_GROUP table. The WEIGHT_ATTRIBUTE 222 table indicates relative importance of attributes within weight groups, and provides default P and PBAR values of attributes when new entities are created. This table also indicates which attributes are to be involved for any transaction that uses the weight group, and which attributes are the most relevant. FIG. 48 shows the specific fields in the WEIGHT_ATTRIBUTE table.

Figure 3:
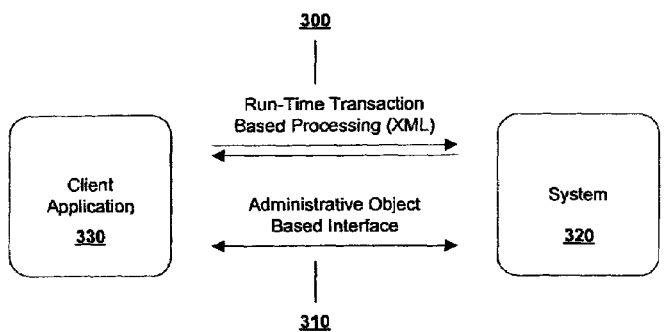
FIG. 3 is a diagram showing the general transactions between the client applications and the system.

There are two basic types of interactions that occur between client applications 330 and the system 320, illustrated in FIG. 3. The first type is a run-time transaction 300 which is used for the sole purpose of matching client entities with the system entities. This transaction 300 is comprised of two or more sets of XML messages passed between the client applications 330 and the system 320. The timing of these messages is controlled by the client applications 330 and a unique transaction ID number references each transaction. The other interaction type is administrative object based interface 310 through which administrative tasks are performed. The interface consists of a small number of object methods and properties and the administrative tasks range from setting up default weighting systems to maintenance of user information such as authentications and access rights.

Figure 4:
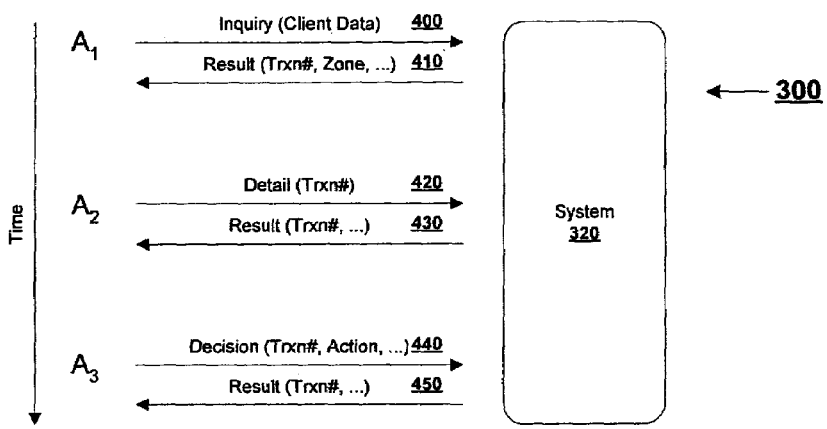
FIG. 4 is a diagram showing the specific steps in a run time transaction
Figure 5:
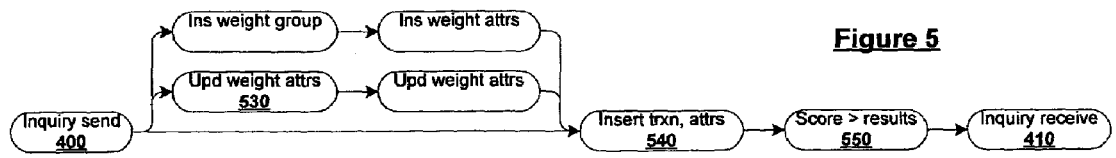
FIG. 5 is a flowchart detailing the steps for processing an inquiry send message and forming the inquiry receive message.

Run time transactions 300 are illustrated in FIG. 4. All messages between the client application 330 and the system 320 employ XML as the communications protocol for all entity matching procedures. The first step in the run time transaction is sending the inquiry send message 400, which contains the client data, to the system 320. Client data is any data sent from an external system to the main system in order to obtain a unique ID. The system 320 processes the information in the inquiry send message 400 and then returns the results of the processing to the client through an administrative tasks 5620 are performed. Finally, the user logs out 5630 and disconnects from the database 150.

i. Inquiry Messaging (illustrated in FIG. 5)

First the client application 330 sends an inquiry send message 500 to the system 320. An inquiry send message 400 is comprised of an indication of the weight group to be used, the attributes associated with that weight group, green and red threshold values, and a list of client attributes. A weight group is an insular collection of attributes given weights relative to each other in order to determine impact on probabilities of matching. Threshold values are values that govern the size of the three zones. At and above the high threshold is the green zone; at and below the low threshold is the red zone; between the high and low thresholds is the yellow zone. Client attributes are any elemental data for a client entity.

Inquiry send messages 400, shown in FIG. 10, are always contained within <INQUIRY> elements (1000, 1040) at the root level. There are three sections to any inquiry send message: the weight group section 1010 (with any optional attributes); the threshold section 1020; and the attributes section 1030.

The weight group specifications follow the railroad diagrams in FIGS. 11–17. Using these diagrams, the following the examples of possible configurations for the weight group specifications can be formed:

```
1. <WEIGHT_GROUP NUMBER="374"/>
2. <WEIGHT_GROUP NAME="TEST GROUP 1"/>
3. <WEIGHT_GROUP NAME="TEST GROUP 1">
    <ATTRIBUTE NAME="LASTNAME" REL="Y" COMPFUNC="ALPHAUPPER" WEIGHT="175" PBAR="0.2"/>
    <ATTRIBUTE NAME="FIRSTNAME" REL="Y" COMPFUNC="ALPHAUPPER" WEIGHT="75" PBAR="0.15"/>
    <ATTRIBUTE NAME="STREET" REL="N" COMPFUNC="ALPHANUMUPPER" WEIGHT="35" PBAR="0.1"/>
    <ATTRIBUTE NAME="CITY" REL="N" COMPFUNC="ALPHANUMUPPER" WEIGHT="25" PBAR="0.08"/>
    <ATTRIBUTE NAME="STATE" REL="N" WEIGHT="15" PBAR="0.05"/>
    <ATTRIBUTE NAME="ZIP" REL="N" COMPFUNC="NUMERIC" WEIGHT="20" PBAR="0.065"/>
</WEIGHT_GROUP>
``` inquiry receive message 410. If the entity matching the initial processing does not produce clear matches, the client application 330 returns further detail in a detail send message. 420 The system 320 again processes the information and send a result back, but this time through a detail receive message 430. Once the entity matching is clear and complete, the user makes a decision based on this information.

The threshold specifications follow the railroad diagram in FIG. 18. The following is an example of a valid threshold specification:

1. <THRESHOLD HIGH="0.6" LOW="0.4"/>

The attribute specifications follow the railroad diagram in FIG. 19. The following are all valid examples of attribute specifications:

```
1. <ATTRIBUTE NAME="LASTNAME" ORIGVALUE="Smith"COMPVALUE="SMITH"/>
2. <ATTRIBUTE NAME="LASTNAME" ORIGVALUE="Smith"COMPFUNC="ALPHAUPPER"/>
3. <ATTRIBUTE NAME="LASTNAME" ORIGVALUE="Smith"/>
```

This decision is sent to the system 320 in a decision send message 440. The system 320 processes this information and sends back the results in a decision receive message 450.

3. Process Flow

Figure 56:
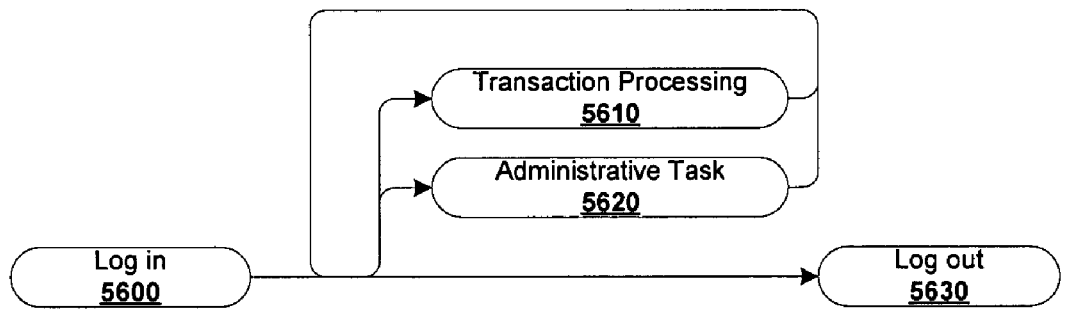
FIG. 56 is a flowchart depicting the general process flow.

Run time transactions 300, administrative transactions 310 and user rights and authentications each fit into the process data flow for the system 320. The process data flow for the system 320 is shown in FIG. 56. This figure shows the typical three step process. The user connects to the database 150 and logs in 5600 via user authentication and encryption. Next, zero or more run time transactions 5610 or As shown, the weight group may already be identified by its unique number (if known) or its unique name. If the weight group already exists in the system 320, specifying attributes for the weight group are optional. But, if attributes are specified, this attribute information will be used to update 530 the stored weight attribute values. If the weight group does not already exist, a new one will be created 540 and information will be stored for each of the attributes listed.

At the same time, new transactions 540 are managed by obtaining a new, unique transaction number from a sequence and inserting a new row in the TRANSACTION table 223 with the weight group number, system user number and greed and red threshold values. New rows are then created in the TRANSACTION_ATTRIBUTE table 224 for each attribute specified in the inquiry send message 400.

Once the data is stored in the database 150, the client data are compressed into a format that can be used for comparisons. Then the scoring algorithm 550 is run and the results are placed in the TRANSACTION RESULT table 225. The potential matches are then computed and stored in the database 150 and indexed in descending order of posterior probability. The posterior probability is the result of all probability calculations that a given known entity is a match for a client.

Next, the inquiry receive message 410 is formed. It includes the transaction number and the resultant zone, which can been green, red or yellow. The green zone indicates a very probable match between a client entity and a known entity and is the high confidence zone. The red zone indicates no probable match with the known entity and is the low confidence zone. The yellow zone indicates that a human decision needs to be made before assigning the client entity a new or existing code and is the indeterminate zone. For green zone results, the iMPI code of the highest match is also returned; for yellow and red zone results, the quantity of potential matches is also returned; this represents the total number of matches above the low threshold. For red zone results, the quantity returned is zero. In all cases, the weight group number is returned as well.

Inquiry receive messages 410, shown in FIG. 20, are always contained within <INQUIRY> elements 2000 at the root level. There are four sections to any inquiry receive message: the transaction number 2010; the zone specification 2020; the quantity of results 2030; and the weight group number 2040.

Figure 6:
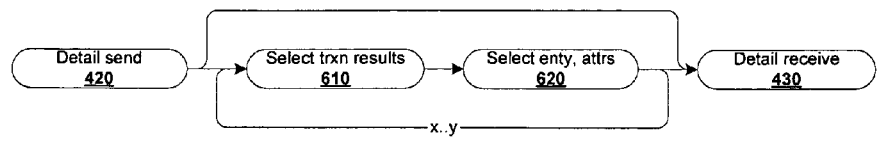
FIG. 6 is a flowchart detailing the steps for processing a detail send message and forming the detail receive message.

The transaction number specification railroad diagram is shown in FIG. 21; the zone specification railroad diagram is shown in FIG. 22; the quantity of results specification is shown in the railroad diagram in FIG. 23; the weight group number specification is shown in the railroad diagram in FIG. 24. The following are examples of valid inquiry receive messages 410:

1. <INQUIRY TRANSACTION_NO="72364" ZONE="G" IMP1_CODE="287364" QUANTITY="4" WEIGHT_GROUP="17"/>
2. <INQUIRY TRANSACTION_NO="72365" ZONE="Y" QUANTITY="9" WEIGHT_GROUP="17"/>
3. <INQUIRY TRANSACTION_NO="72366" ZONE="R" QUANTITY="0" WEIGHT_GROUP="31"/> ii. Detail Messaging (illustrated in FIG. 6)

Detail messages 420 are used for yellow zone results and for green zone results in cases where the client application 330 wishes to review more options instead of automatically selecting the highest scoring match. The detail send message 420 is comprised of a transaction number, which is used to direct the system 320 to the appropriate results. Also included are result index numbers which direct the system 320 to return only the desired results. The first number is the lower result index bound of the subset and the second number is the upper result index bound of the subset.

Detail send messages 420, shown in FIG. 25, are always contained in <DETAIL> elements 2500 at the root level. There are three parts to a detail send message 420: the transaction number 2510; the lower result index bound 2520; the upper result index bound 2530.

The transaction number specification railroad diagram is shown in FIG. 26; the lower result index bound specification railroad diagram is shown in FIG. 27; the upper result index bound specification railroad diagram is shown in FIG. 28. Following these diagrams, a valid detail send message 420 can be formed, such as:

1.<DETAIL TRANSACTION_NO="32" FIRST="2" LAST="3"/>

Next, the transaction results 610 from the inquiry message are selected from the database 150 and for each result with an index between the bounds, the posterior probability, iMPI code, and attributes are selected 620 from the database 150.

Finally, with these results a detail receive message 430 is created containing the unique transaction number and information from each of the results returned including posterior probability, iMPI code of the know entity, and all of the known entity's attributes.

Figure 29:
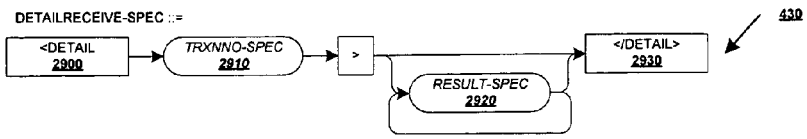
FIG. 29 is a railroad diagram detailing the formation of XML code for detail receive messages.

Detail receive messages 430, shown in FIG. 29, are always contained within <DETAIL> elements (2900, 2930) at the root level. A detail receive message 430 contains the transaction number 2910 and zero or more results 2920.

Figure 30:
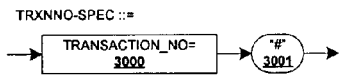
FIG. 30 is a railroad diagram detailing the formation of XML code for transaction number specification for detail receive messages.
Figure 31:
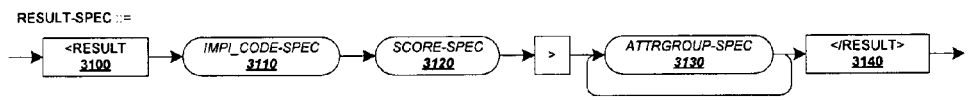
FIG. 31 is a railroad diagram detailing the formation of XML code for result specification for detail receive messages.
Figure 32:
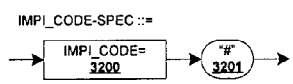
FIG. 32 is a railroad diagram detailing the formation of XML code for iMPI code specification for detail receive messages.
Figure 33:
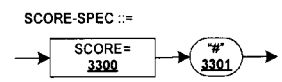
FIG. 33 is a railroad diagram detailing the formation of XML code for score specification for detail receive messages.
Figure 34:
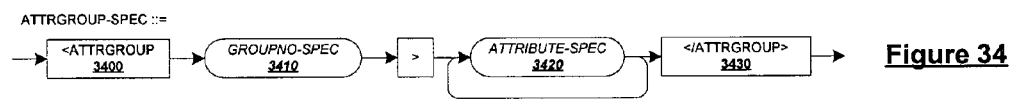
FIG. 34 is a railroad diagram detailing the formation of XML code for attribute group specification for detail receive messages.
Figure 35:
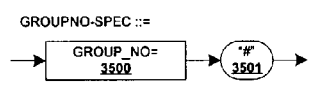
FIG. 35 is a railroad diagram detailing the formation of XML code for group number specification for detail receive messages.
Figure 36:
FIG. 36 is a railroad diagram detailing the formation of XML code for attribute specification for detail receive messages.
Figure 37:
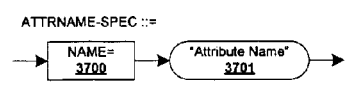
FIG. 37 is a railroad diagram detailing the formation of XML code for attribute name specification for detail receive messages.
Figure 38:
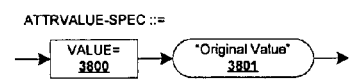
FIG. 38 is a railroad diagram detailing the formation of XML code for attribute value specification for detail receive messages.

The transaction number specification railroad diagram is shown in FIG. 30. The results specification railroad diagram is shown in FIG. 31. Each result contains an iMPI code 3110, the posterior probability (or score) 3120 and all the attributes 3130 stored for the entity in descending order of group number. The iMPI code specification railroad diagram is shown in FIG. 32 and the score railroad diagram is shown in FIG. 33. The attribute specification railroad diagram is shown in FIGS. 34–38. Following these railroad diagrams, a valid detail receive message 430 can be created, such as:

1.
<DETAIL TRANSACTION_NO="32">
    <RESULT IMPI_CODE="12343" SCORE="0.8">
        <ATTRGROUP GROUP_NO = "8229">
            <ATTRIBUTE NAME="LASTNAME" VALUE="Smith">
            <ATTRIBUTE NAME="FIRSTNAME" VALUE="Joe">
            <ATTRIBUTE NAME="ZIPCODE" VALUE="87401">
        </ATTRGROUP>

-continued

<ATTRGROUP GROUP_NO = "1712">
    <ATTRIBUTE NAME="LASTNAME" VALUE="Smith">
    <ATTRIBUTE NAME="FIRSTNAME" VALUE="Joseph">
    <ATTRIBUTE NAME="ZIPCODE" VALUE="87401">
</ATTRGROUP>
<ATTRGROUP GROUP_NO = "1">
    <ATTRIBUTE NAME="LASTNAME" VALUE="Smith">
    <ATTRIBUTE NAME="FIRSTNAME" VALUE="J">
    <ATTRIBUTE NAME="ZIPCODE" VALUE="87401">
</ATTRGROUP>
/RESULT>
RESULT IMPI_CODE="22344" SCORE="0.79">
    <ATTRGROUP GROUP_NO = "9928">
        <ATTRIBUTE NAME="LASTNAME"
            VALUE="Williams">

-continued

```
        <ATTRIBUTE NAME="FIRSTNAME" VALUE="John">
        <ATTRIBUTE NAME="ZIPCODE" VALUE="87410">
      </ATTRGROUP>
      <ATTRGROUP GROUP_NO = "2091">
        <ATTRIBUTE NAME="LASTNAME"
        VALUE="Williams">
        <ATTRIBUTE NAME="FIRSTNAME" VALUE="J">
        <ATTRIBUTE NAME="ZIPCODE" VALUE="87401">
      </ATTRGROUP>
   </RESULT>
</DETAIL>
``` iii. Decision Messaging

The client application 330 delivers a decision to the system 320 via a decision send message 440.

Figure 39:
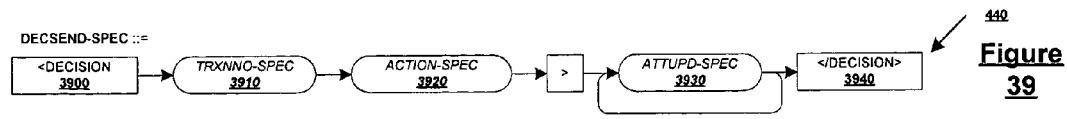
FIG. 39 is a railroad diagram detailing the formation of XML code for decision send messages.

Decision send messages 440, shown in FIG. 39, are always contained with <DECISION> elements at the root level. Decision send messages 440 include the transaction number 3910 and an action specification 3920. In the case of done messages, no attribute specification 3930 is required.

Figure 40:
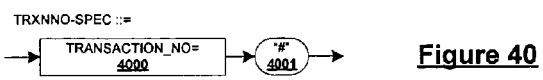
FIG. 40 is a railroad diagram detailing the formation of XML code for transaction number specification for decision send messages.
Figure 41:
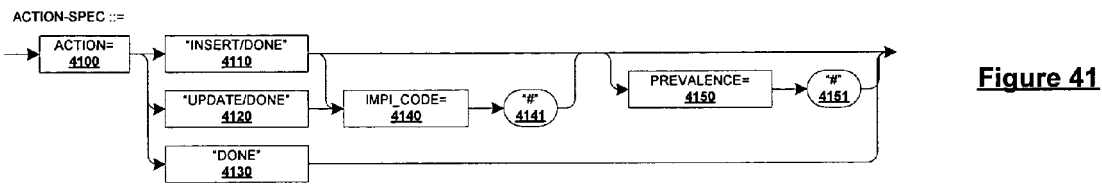
FIG. 41 is a railroad diagram detailing the formation of XML code for action specification for decision send messages.
Figure 42:
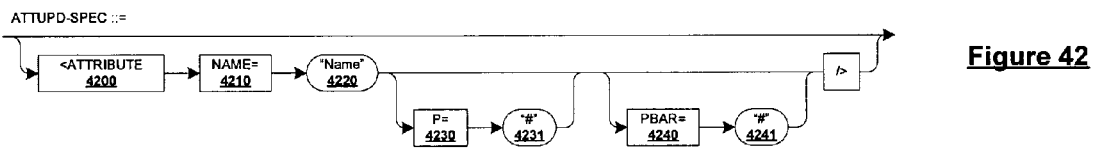
FIG. 42 is a railroad diagram detailing the formation of XML code for attribute specification for decision send messages.

The transaction number specification railroad diagram is shown in FIG. 40. The action specification railroad diagram is shown in FIG. 41. The attribute specification railroad diagram is shown in FIG. 42. Using these diagrams, the following valid examples of decision send messages 440 can be formed:

attributes impact on a match given a mismatch with the value sought. The system 320 receives the insert/done message 701 and determines that new entity 710 and attribute information 740 must be inserted into the ENTITY 228 and ATTRIBUTE 226 tables. The system 320 creates new rows in each of these tables and inserts the information passed in the inquiry send message 400. When a prevalence value is specified, it is applied to the new row in the ENTITY 228 table; when not specified, the values are taken from the appropriate row in the WEIGHT_ATTRIBUTE 222 table. When P or Pbar values are specified, they are applied to the appropriate row in the ATTRIBUTE_COMPUTATION_VALUE 227 table; when not specified, the values are taken from the appropriate row in the WEIGHT_ATTRIBUTE 222 table.

If the requested action is update/done 702, the decision send message 440 includes a transaction number, the decision code corresponding to an insert/done 701 action, and iMPI number and could include Prevalence values, P values and Pbar values. The system 320 receives the update/done message and determines that a new attribute group 740 needs to be inserted for an already existing entity corresponding to the iMPI code passed in this message. When a prevalence value is specified, it is applied to the new row in the ENTITY 228 table; when not specified, the values are taken from the appropriate row in the WEIGHT_ATTRIBUTE 222 table. When P or Pbar values are specified, they are applied to the appropriate row in the ATTRIBUTE_

```
1.
<DECISION TRANSACTION_NO="2" ACTION="INSERT/DONE" PREVALENCE="0.16">
<ATTRIBUTE NAME="LASTNAME" P="0.32" PBAR="0.252">
<ATTRIBUTE NAME="FIRSTNAME" P="0.09">
<ATTRIBUTE NAME="STREET" PBAR="0.125">
</DECISION>
2. <DECISION TRANSACTION_NO="8276" ACTION="INSERT/DONE"/>
3.
<DECISION TRANSACTION_NO="2" ACTION="UPDATE/DONE" IMPI_CODE="8746" PREVALENCE="0.16">
<ATTRIBUTE NAME="LASTNAME" P="0.32" PBAR="0.252">
<ATTRIBUTE NAME="FIRSTNAME" P="0.09">
<ATTRIBUTE NAME="STREET" PBAR="0.125">
</DECISION>
4. <DECISION TRANSACTION_NO="194587" ACTION="UPDATE/DONE" IMPI_CODE="8746"/>
5. <DECISION TRANSACTION_NO="29237" ACTION="DONE"/>
```

Figure 7:
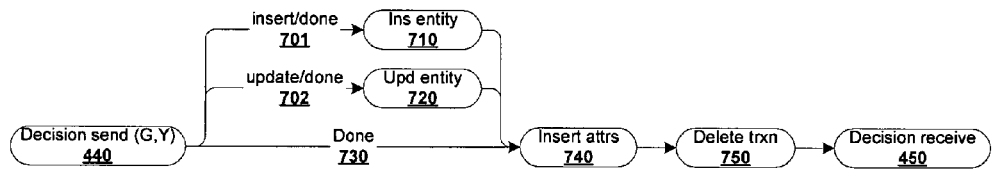
FIG. 7 is a flowchart detailing the steps for processing a decision send message and forming the decision receive message for green and yellow zone results.

Green or Yellow Results (illustrated in FIG. 7)

The decision send message 440 for a green or a yellow result can request one of three actions: insert/done, update/done or done. Insert/done actions instruct the system 320 to insert a new known entity and its attributes into the database 150. The attribute values inserted are the attribute values passed in via the inquiry send message 400. Update/done actions instruct the system 320 to insert a new attribute group into the database 150 for an already existing entity. The existing entity is identified by the code passed in the decision send message 440. Done actions simply instruct the system 320 to delete the transaction entirely without taking any other action.

If the requested action is insert/done 701, the decision send message 440 includes a transaction number, the decision code corresponding to an insert/done action, and iMPI number and could include Prevalence values, P values and Pbar values. P values are probabilistic contribution factors that determine an attribute's impact on a match given the presence of the value sough. On the other hand, Pbar values are probabilistic contribution factors that determine an COMPUTATION_VALUE table; when not specified, the values are taken from the appropriate row in the WEIGHT_ATTRIBUTE 222 table.

If the requested action is "done" 730, no rows in the ENTITY 228, ATTRIBUTE 226 or ATTRIBUTE_COMPUTATION_VALUE 227 tables are affected in any way.

After each of the three above actions, the transaction is then deleted 750 from the TRANSACTION 223, TRANSACTION_ATTRIBUTE 224 and TRANSACTION_RESULT 225 tables.

A decision receive message 450 consisting of the transaction number, a pass/fail code and if the action requested was insert/done, the iMPI number for the new entity, is passed then back to the user.

Figure 43:
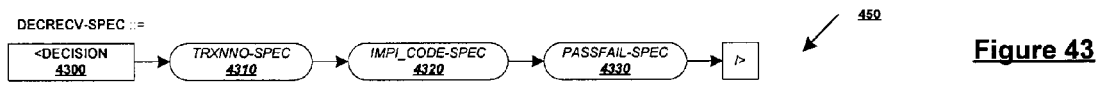
FIG. 43 is a railroad diagram detailing the formation of XML code for decision receive messages.

Decision receive messages 450, shown in FIG. 43, are always contained within <DECISION> elements at the root level. There are at most three sections to any decision receive message 450: the transaction number 4310, the iMPI code 4320 (in the case of insert/done messages only); and the pass/fail code 4330.

Figure 44:
FIG. 44 is a railroad diagram detailing the formation of XML code for transaction number specification for decision receive messages.
Figure 45:
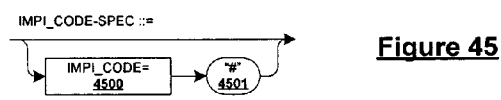
FIG. 45 is a railroad diagram detailing the formation of XML code for iMPI code specification for decision receive messages.
Figure 46:
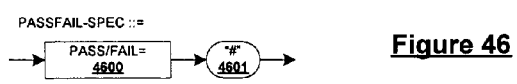
FIG. 46 is a railroad diagram detailing the formation of XML code for pass fail code specification for decision receive messages.

The transaction number specification railroad diagram is shown in FIG. 44. The iMPI code specification railroad diagram is shown in FIG. 45 and the pass fail code specification railroad diagram is shown in FIG. 46. Using these railroad diagrams, the following valid examples of decision receive messages 450 can be constructed:

1. <DECISION TRANSACTION_NO="8237" PASS/FAIL="0"/>

2. <DECISION TRANSACTION_NO="2" IMPI_CODE="38737" PASS/FAIL="0"/>

3. <DECISION TRANSACTION_NO="2" PASS/FAIL="1"/>

Figure 8:
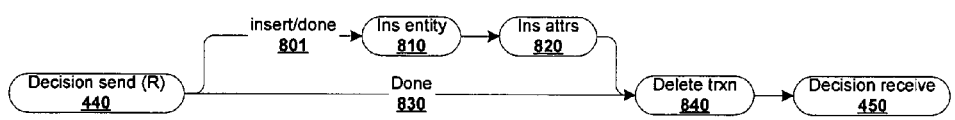
FIG. 8 is a flowchart detailing the steps for processing a decision send message and forming the decision receive message for red zone results.
Figure 9:
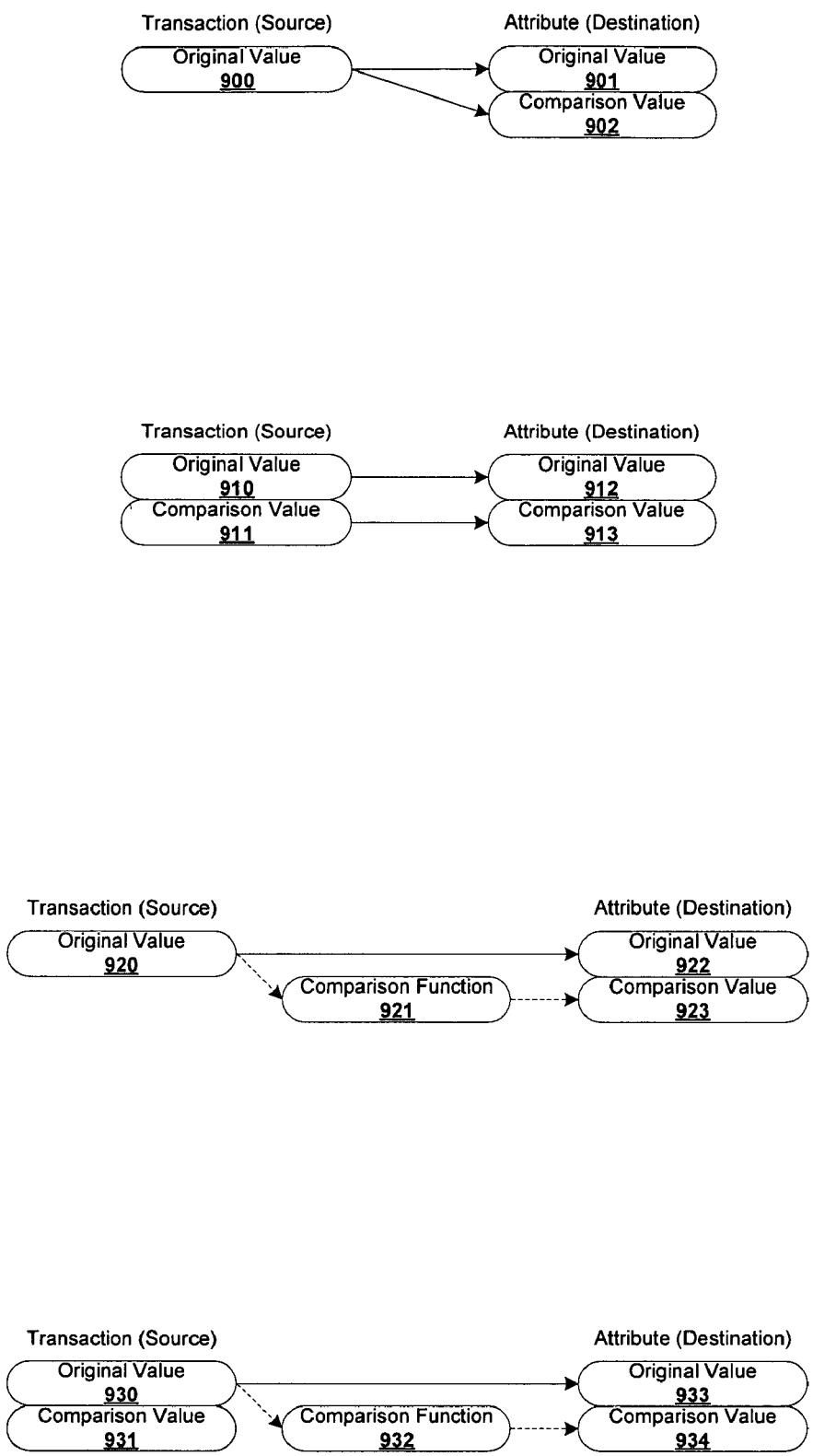
FIG. 9 is a flowchart showing the numerous ways original and comparison values are determined for insertion in the attribute table.

Red Results (illustrated in FIG. 8)

The client application 330 delivers a decision to the system 320 via a decision send message 440. The decision send message 440 can request one of two actions.

If the requested action is insert/done 801, the same procedure is followed as in the insert/done action processed for a green or yellow result. (810,820)

If the requested action is done, the same procedure is followed as in the insert/done action processed for a green or yellow result, without the attribute insertion step. (830)

After each of these two actions, the transaction is then deleted from the TRANSACTION 223, TRANSACTION_ATTRIBUTE 224 and TRANSACTION_RESULT 225 tables.

A decision receive message 450 consisting of the transaction number, a pass/fail code and if the action requested was insert/done, the iMPI number for the new entity, is passed back to the user. A pass fail code of zero indicates success; any other pass fail code indicates failure of some kind.

4. Comparison Functions

When a client application 330 passes attribute values to the system 320 during a transaction, a comparison value or comparison function may be specified. A comparison value is a value that is formatted for comparison with the data in the system 320. A comparison function is an algorithm that is used to convert values from their original format to a format for comparison with data in the system 320.

If no comparison value or comparison function is specified, the system 320 uses the original value 900 passed to it in the transaction to populate the original value 901 and comparison value 902 fields in the ATTRIBUTE 226 table.

If both an original value 910 and a comparison value 911 are specified in the transaction, the original value 910 is used to populate the original value 912 field in the ATTRIBUTE table 226, and the comparison value 911 is used to populate the comparison value 913 field in the ATTRIBUTE 226 table.

If an original value 920 and a comparison function 921 are specified, the original value 920 is used to populate the original value 922 field in the ATTRIBUTE 226 table and the original value 920 is processed by the comparison function 921 whose output is used to populate the comparison value 923 field in the ATTRIBUTE 226 table.

If an original value 930, a comparison value 931 and a comparison function 932 are specified the following occurs: The original value 930 is used to populate the original value 933 field in the ATTRIBUTE 226 table and the original value 930 is processed by the comparison function 932 whose output is used to populate the comparison value 934 field in the ATTRIBUTE 226 table. The comparison value 931 passed in is not used.

Numerous comparison functions can be built into the system 320 and used to process original values. For example, a comparison function that processes an original value and retains and uppercases only alphabetic characters can be built into the system 320. Furthermore, a comparison function can be incorporated that retains and uppercases only alphanumeric characters. Also, functions can be incorporated that retain only numeric and associated characters, or convert values to standard soundex function values consisting of a single uppercase character followed by three numeric digits.

EXAMPLE

Figure 57:
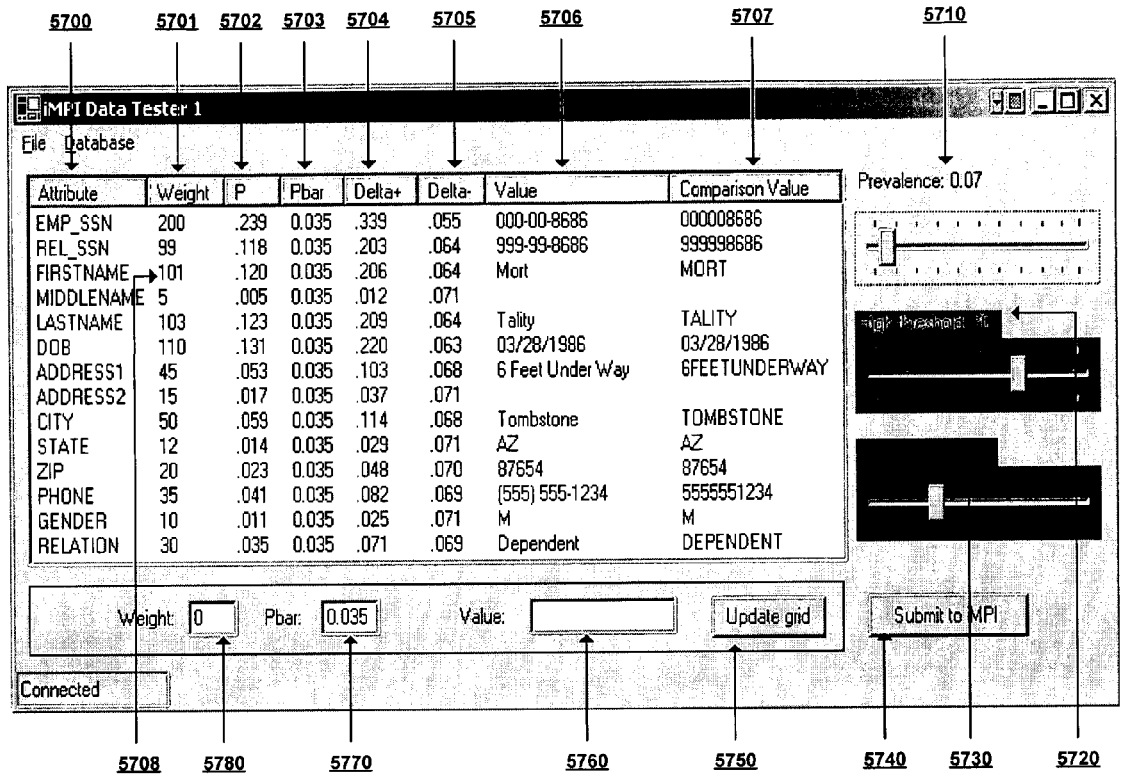
FIG. 57 is a screenshot showing a client entity and its associated attributes.

An example of the above process flow is shown in FIGS. 57–60. In FIG. 57, a client entity and its attributes 5700 are listed. Each attribute 5700 has a corresponding weight 5701, P value 5702, Pbar value 5703, positive Delta value 5704, negative Delta value 5705, original value 5706 and comparison value 5707. The delta values 5704, 5705 represent the effect a positive or negative match on that attribute 5700. Furthermore, the prevalence value 5710, upper zone threshold 5720 and lower zone threshold 5730 are defined and are adjustable by the client. With the settings shown in FIG. 57, the red zone is defined by a score between 0 and 0.3 and the green zone is defined as a score above 0.7. The yellow zone represents a score between 0.3 and 0.7. The values associated with each attribute 5700 are adjustable as well. By selecting one of the attributes 5700 and an associated field 5701, 5702, 5703, the client is able to change the values by using fields 5760, 5770 and 5780. By clicking the update grid button 5750, the results are updated on the grid screen 5790. To perform the computation of a score, the submit to iMPI button 5740 is clicked.

Figure 58:
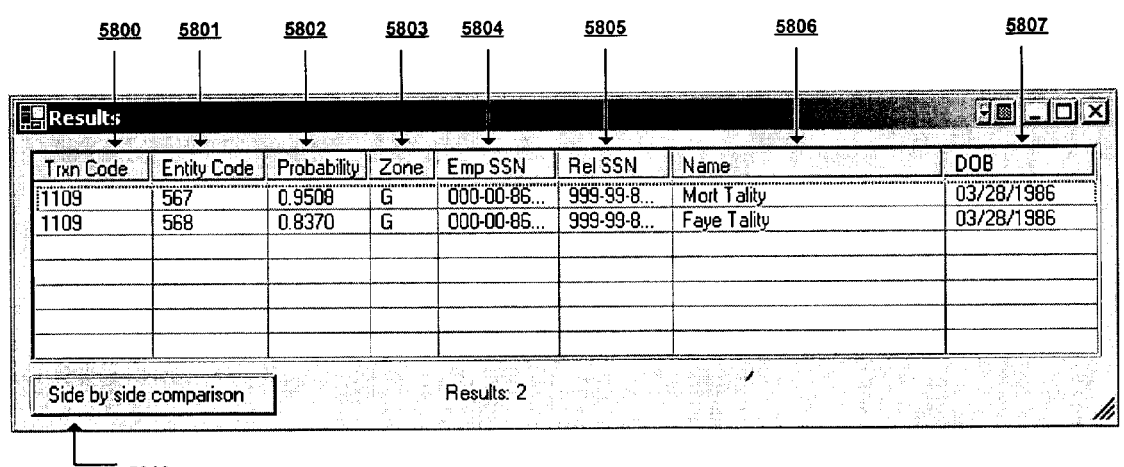
FIG. 58 is a screenshot showing the score results of a matching computation.

FIG. 58 shows the results of the processing by the system 320. On this screen, the scores 5802 and the resultant zones 5803 are shown. The client can determine a match based on the results if there is only one green zone result or if there are no green or yellow results. In the example shown in FIG. 58 there are two green zone results with high scores. The client can view these results in more detail by clicking the side by side comparison button 5810.

FIGS. 59 and 60 show the side by side comparisons for the two matches shown in FIG. 58. Viewing these comparisons, the client can determine that these entities are twins and determine which twin is the correct match. With this knowledge, the client can adjust the weight of the first name field 5808, thereby increasing its contribution to the scoring algorithm.

5. Scoring Algorithm

In order to determine the best (if any) match between a client entity and an existing entity, a powerful algorithm called a multi-membership Bayesian computation is used. This computation uses multimember probabilities to determine the likelihood, or confidence, that a particular client entity and a known system entity are one and the same.

When matching a client entity with an existing entity, the attributes of the client entity are compared with the attributes of all known system entities.

Each entity is described by of a number of attributes. In one embodiment, the entity could represent a person, while the attributes represent first name, last name, social security number, etc. Different data sources may supply different attributes, but it is the process of matching client attributes against the attributes of known system entities that determines the best match and the confidence of the match.

Each set of attributes used for comparison is initially represented in the WEIGHT_GROUP 221 and WEIGHT_ATTRIBUTE 222 tables in the database 150. The WEIGHT_GROUP 221 table provides a default prevalence value that is copied to the ENTITY 228 table upon row creation and provides the starting point for all probability calculations on that entity. The WEIGHT_ATTRIBUTE 222 table provides a listing of all attributes in the weight group. For each attribute, a name (unique to that group), a relevance flag, comparison function, relative weight, P, and PBAR values are stored. Many of these values are copied to the ATTRIBUTE_COMPUTATION_VALUE 227 table upon creation of an entity.

Attributes within a group are given integer weights relative to each other. Higher weights indicate attributes that contribute more weight in the computations. Each attribute's listed weight is relative to the other attributes in the weight set, each attribute has a value computed as a percentage of its weight against the sum of the weights in the group. This value is called P, and represents the attribute's contribution to the posterior probability where a match is present.

In one embodiment the entity might represent a person and the attributes associated with that entity are first name, last name and social security number. Therefore, system entity A might be represented by first name=John, last name=Doe and social security number=123456789. System entity B might be represented by first name=John, last name=Orangopulos and social security number=123454321. For entity A, John might have an integer weight of 10, Doe, a weight of 10 and 123456789 a weight of 30. For entity B, John might have an integer weight of 10, Orangopulos, a weight of 30 and 123454321, a weight of 10. Since P values are relative based on the integer weights, the social security number value in entity A has 0.6 contribution, while the first name and last name values contribute only 0.2 each to the posterior probability. Similarly for entity B, the last name field would have a P value of 0.6, while the first name and social security number values would have P values of 0.2 each.

The probability that a client entity is the same as a known system entity is based on which attributes of the transaction entity match which attributes of the known entity, which attributes do not and which attributes are not available. When attribute values are available for comparison, and a match is not made, a value associated with the system attribute is detracted from the posterior probability. The detraction value is the PBAR value. In the system 320 a default PBAR value is set and this value is adjusted in either direction for any attribute for any given weight set, depending on the statistical quality of data that weight set is intended to represent. These adjustments must be made before any scoring process using the weight set begins. The P and PBAR values are both factored into the computation of the posterior probabilities and will result in a probability between 0 and 1.

i. Scoring Steps

The first step in matching entities is to look at the client values for all attributes flagged as relevant. A flag is included in the WEIGHT_ATTRIBUTE 222 table to indicate which attributes the client considers the most relevant. These attributes may not necessarily have the highest contributions; attributes with this flag set are merely used to determine a starting set of entities with which to compare client data to system data. Only known entities matching at least one of the most relevant attributes will be considered for further calculations.

For each known entity in the most relevant match set, each attribute of the client entity is compared and contrasted to the known entity attributes. If the attribute values are a positive match, the attribute value's P value is contributed to the computation. If the attribute values are a negative match, the attribute value's PBAR value is contributed to the computation. If there is no client data for a known attribute, there is no contribution to the computation. A multi-membership Bayesian formula is applied in order to compute the posterior probabilities for each of the known entities in the most relevant match set.

The Bayesian formula to compute the posterior probability for each entity is represented by the ComputeBayesian Value function.

```
public decimal ComputeBayesianValue(decimal fparPrev)
{
    decimal fNum = 0.0m;
    decimal fDen = 0.0m;
    TTransactionAttribute taTemp;
    fNum = fparPrev;
    fDen = (1 - fparPrev);
    for (int i=0; i<Attributes.Count; i++)
    {
        taTemp = Attributes.Objects(i) as
        TTransactionAttribute;
        if ((taTemp.iHit == 1) && (taTemp.fP > 0) &&
        (taTemp.fPbar > 0))
        {
            fNum = fNum * taTemp.fP;
            fDen = fDen * taTemp.fPbar;
        }
        else if ((taTemp.iHit == -1) && (taTemp.fP > 0) &&
        (taTemp.fPbar > 0))
        {
            fNum = fNum * (1 - taTemp.fP);
            fDen = fDen * (1 - taTemp.fPbar);
        }
    }
    return fNum / (fNum + fDen);
}
```

This function takes the prevalence value as input. First, it sets the default numerator value (fNum) equal to the prevalence value and the default denominator contributing value (fDen) as one minus the prevalence value. The function then enters a loop of all the attributes passed in by the client application. At this point, the attributes have been compared to the entities attributes and assigned an iHit value. If there was a match, the iHit value is set to 1 and if there was no match, the iHit value is set to −1. Within the loop, the iHit value determines which function is used to update the fNum and fDen values. This allows for both positive and negative contributions to the posterior probability. Also, this function allows no contribution if information about a certain attribute is missing. Once the loop is completed the posterior probability is returned.

6. Administrative Tasks

Figure 55:
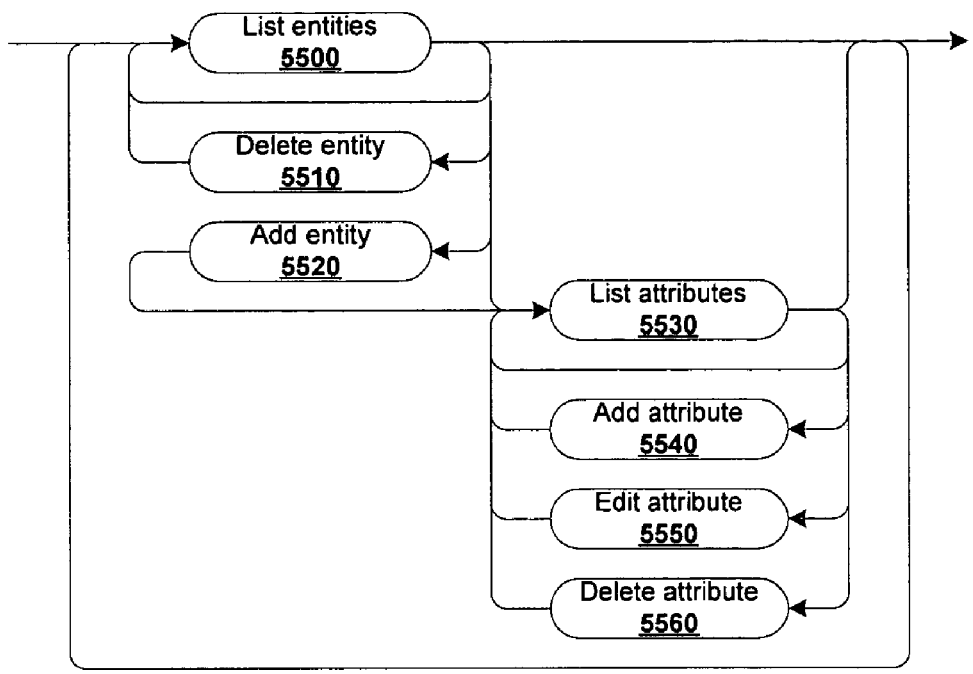
FIG. 55 is flowchart depicting the typical known entity application flow.

System administration tasks 310 are performed in all areas of the system 320. These tasks are not transaction based, but rather encapsulated into single functions. Various methods and properties built into the system interfaces allow client applications 330 to perform these tasks independently of each other. The general, but non-exhaustive types of tasks allowed via an interface are entity tasks, user tasks, weight group tasks and transaction tasks. FIG. 55 shows a railroad diagram for a typical application flow for maintenance of known entities. The tasks allow client applications 330 to list sets and subsets of known entities 5500, and to also add 5520 or delete 5510 these sets and subsets of known entities. For the attributes, the client application 330 can list 5530 all of the attributes for a known entity and add 5540, edit 5550 or delete 5560 these attributes. The other general types of tasks allowed by the system 320 allow for similar updating and editing functionality. Where possible, the majority of functionality for any given task or set of tasks should be performed through an interface property. This property may be indexed as necessary and should generally follow these simple guidelines: When assigning a non-null value to a property, if index value exists, overwrite old property value(s) for that item. If the index value does not exists, add index value and assign property value(s) provided. When assigning a null value to a property, delete the index value and associated property value(s).

7. User Rights and Authentications

The system 320 makes use of authentications and permissions technology developed with ADM. This allows the system managers to specify how each user may log in to the application and which functionality each user has access to. Users may have explicit authentications, meaning that they must supply a password, or domain-based authentications, meaning that their operating system domain will be automatically detected and login effected transparently to the user. Also, permissions are defined for various functionalities within the system 320. Where these permissions are granted, users may perform tasks. Where they are not granted, users are prevented form performing tasks such as inserting and updating new entities, modifying weight groups, attributes and data on other users as well as accessing event log data.

What is claimed is:

1. A method operable on one or more computers for mapping and identifying entity information in a system including a database comprising:

sending client entity attributes from a client application to said system;

comparing said client entity attributes with attributes of system entities stored in said system;

calculating scores for relevance between said client entity and said system entities using a multi-membership Bayesian probability function;

classifying said relevance scores in accordance with predetermined threshold values;

creating an alias containing said client entity attributes;

either pointing said alias to a selected system entity, or creating a new system entity and pointing said alias to said new system entity; and wherein said calculating step using said multi-membership Bayesian probability function utilizes positive, negative and neutral contributions to said score depending on the results of said comparing step.

2. A method according to claim 1 wherein said sending step uses XML communications protocol.

3. A method according to claim 1 wherein said sending step can specify said client entity attributes, for use in said comparing step, by a group defined in said system.

4. A method according to claim 1 wherein said classifying step utilizes a high confidence zone, a low confidence zone and an indeterminate zone.

5. A method according to claim 1 wherein said client entities and system entities represent persons.

6. A method according to claim 1 wherein said system is a master patient index.

7. A method according to claim 1 further including converting client entity attributes into a format suitable for said comparing step.

8. A method according to claim 1 wherein said calculating step includes assigning weights to attributes when comparing client entity attributes and system entity attributes, such that certain attributes contribute more or less to the score of said calculating step.

9. A method according to claim 8 wherein the weights assigned to attributes are source-dependant.

10. A method according to claim 1 wherein during said calculating step, a score is calculated for only those system entities in which at least one of a predetermined set of attributes has a value matching that of a corresponding client entity attribute.

* * * * *